US 6,629,933 B1

(12) United States Patent
Lindner

(10) Patent No.: US 6,629,933 B1
(45) Date of Patent: Oct. 7, 2003

(54) METHOD AND DEVICE FOR DETERMINING PER BREATH THE PARTIAL PRESSURE OF A GAS COMPONENT IN THE AIR EXHALED BY A PATIENT

(75) Inventor: Bernd Lindner, Ratekau (DE)

(73) Assignee: Envitec Wismar GmbH, Wismar (DE)

( * ) Notice: Subject to any disclaimer, the term of this patent is extended or adjusted under 35 U.S.C. 154(b) by 0 days.

(21) Appl. No.: 09/959,424

(22) PCT Filed: Apr. 25, 2000

(86) PCT No.: PCT/EP00/03689

§ 371 (c)(1),
(2), (4) Date: Jan. 28, 2002

(87) PCT Pub. No.: WO01/80735

PCT Pub. Date: Nov. 1, 2001

(51) Int. Cl.[7] ................................................. A61B 5/08
(52) U.S. Cl. ......................... 600/532; 600/529; 73/23.3; 422/84
(58) Field of Search ................................ 600/529, 531, 600/532, 300–301; 73/23.3; 422/84

(56) References Cited

U.S. PATENT DOCUMENTS

| 3,523,529 A | * | 8/1970 | Kissen | 600/531 |
| 4,359,057 A | | 11/1982 | Manzella | |
| 4,572,208 A | | 2/1986 | Cutler et al. | |
| 4,728,499 A | | 3/1988 | Fehder | |
| 5,117,674 A | * | 6/1992 | Howard | 73/31.07 |
| 5,533,512 A | * | 7/1996 | Novotny et al. | 600/532 |
| 5,705,735 A | * | 1/1998 | Acorn | 73/23.3 |
| 6,478,736 B1 | * | 11/2002 | Mault | 600/300 |

FOREIGN PATENT DOCUMENTS

| DE | 40 01 803 | 7/1991 |
| EP | 0 392 503 | 10/1990 |
| GB | 2 084 321 | 4/1982 |
| WO | WO 93/00040 | 1/1993 |
| WO | WO 99/39637 | 8/1999 |

OTHER PUBLICATIONS

Form PCT/IB/338 and Form PCT/IPEA409 from International Application No. PCT/EP00/03689, filed Apr. 25, 2000.
Garnett, A.R. et al., "End–Tidal Carbon Dioxide Monitoring During Cardiopulmonary Resuscitation," *JAMA* 257(4): 512–515 (Jan. 1987).
MacLeod, G.J. et al., "Verification of Endotracheal Intubation Using a Disposable End–Tidal $CO_2$ Detector," *Prehospital and Disaster Medicine* 4(1): 74 (Jul. 1989).
Heller, M.B. et al., "End–Tidal $CO_2$ Detection," *Annals of Emergency Medicine* 18: 1375 (Dec. 1989).
Sanders, A.B., "Capnometry in Emergency Medicine," *Annals of Emergency Medicine* 18: 1287–1290 (Dec. 1989).

* cited by examiner

Primary Examiner—Robert L. Nasser
Assistant Examiner—Patricia Mallari
(74) Attorney, Agent, or Firm—Shanks & Herbert

(57) ABSTRACT

The invention relates to an inexpensive method in which the partial pressure of a gas component in the air exhaled by a patient is determined per breath.

7 Claims, 4 Drawing Sheets

METHOD AND DEVICE FOR DETERMINING PER BREATH THE PARTIAL PRESSURE OF A GAS COMPONENT IN THE AIR EXHALED BY A PATIENT

This application claims benefit under 35 U.S.C. 371 to International Application No. PCT/EP00/03689, filed Apr. 25, 2000. International Application No. PCT/EP00/03689 was published under PCT Article 21(2) in German.

FIELD OF THE INVENTION

The invention relates to a method and a device for determining per breath the partial pressure of a gas component in the respiratory air of a patient, to be more exact a method for determining the $CO_2$ content in the respiratory air, and a ventilation device which is designed such that the method can be carried out using it.

BACKGROUND OF THE INVENTION

In medicine, the carbon dioxide content in respiratory air can be used to draw important conclusions concerning the state of health of a patient and possible medical conditions. In addition to the absolute content (or the partial pressure) of the carbon dioxide in the exhaled air, the $CO_2$ curve shape is important (corresponding curves in which the $CO_2$ content (or partial pressure) is plotted against time are referred to as capnograms), particularly also whether the maximum value of the carbon dioxide content in the exhaled air rises, falls or remains constant during the respiratory cycles and at what speed it rises or falls. These types of information are particularly important if a patient is intubated and artificially ventilated, for example under general anaesthesia, but also in emergency medicine and during spontaneous ventilation.

FIG. 1 illustrates a number of examples of typical capnograms. Of these, FIG. 1a) shows the capnogram of a healthy patient under controlled ventilation. The maximum $CO_2$ content in the exhaled air is about 5%. FIG. 1b) shows the capnogram of a patient in whom the normal $CO_2$ curve falls to 0 from one breath to the next. This can be caused, for example, by a disconnection of the ventilator from the patient, or there may have been a complete airway obstruction, caused for example by a completely blocked endotracheal tube. FIG. 1c) shows a rapid and constant fall of the $CO_2$ content in the exhaled air and may be an indication of a significant pulmonary air embolism, a cardiac arrest or severe hypotension. In FIG. 1d) the carbon dioxide content in the exhaled air suddenly falls to a lower level, but not to 0, and remains constant at said level. This is caused for example by shifting of the endotracheal tube into a bronchus, for example when changing the position of the patient, or by a sudden partial airway obstruction. A capnogram also provides indications of the onset of hyperventilation, a fall in cardiac output or pulmonary perfusion, onset of hypoventilation, increasing energy conversion rate as a consequence of pain or fever, inadvertent intubation of the stomach instead of the lung, malignant hyperthermia, inadequate muscle relaxation and inadequate depth of anaesthesia and other serious or life-threatening conditions of the patient.

Even when a complete capnogram is unavailable, it is still possible to use the development of the maximum carbon dioxide content in the exhaled air over a number of respiratory cycles to obtain valuable information on possibly serious or life-threatening conditions of a patient. Corresponding trend curves, as they are known, are shown in FIG. 2. In FIG. 2a) the patient is initially stable and the maximum content of the carbon dioxide in the exhaled air is about 5%. However, the maximum content of the carbon dioxide in the exhaled air suddenly falls off rapidly. Possible causes for this are a cardiopulmonary bypass, cardiac arrest, pulmonary embolism, great loss of blood, or an extremely abrupt drop in blood pressure. FIG. 2b) shows a constantly low maximum carbon dioxide content in the exhaled air, at just under 4%. Possible causes for this are hyperventilation caused by too high a minute volume or a low body temperature following shock. FIG. 2c) shows the sudden fall in the maximum value of the carbon dioxide content in the exhaled air to about 0. Possible causes for this are accidental extubation, total airway obstruction, disconnection or oesophageal intubation. In the event of oesophageal intubation, the drop to 0 occurs after just one to two respiratory cycles. FIG. 2d) shows a gradual rise in the maximum value of the $CO_2$ concentration in the exhaled air, possibly caused by an increase in metabolism and body temperature, incipient hypoventilation, or by a decrease in effective alveolar ventilation . FIG. 2e) shows the trend curve in the case of a sudden drop in the maximum value of the carbon dioxide content in the exhaled air, for example as a result of leakage in the tube system, a partial airway obstruction, or a tube in the hypopharynx. FIG. 2f) shows a constantly high maximum value of the carbon dioxide in the exhaled air, possible causes of which are respiratory depression caused by medication, metabolic alkalosis (respiratory compensation) or an inadequate minute ventilation.

Concerning determination of $CO_2$ in exhaled air in medicine, reference can be made to the "Annals of Emergency Medicine" 1989, 1287/53 to 1290/56, "Annals of Emergency Medicine" 1989, 166/1375, "Prehospital and Disaster Medicine" Vol. 4, # 1, 1989, page 74, and "JAMA" 1987, Vol. 257, No. 4, 512 to 515.

Devices for determining the carbon dioxide content in exhaled air are known and are widely used in medicine. These devices must be able to respond rapidly to changes in the $CO_2$ content in the exhaled air, and the devices generally used for this purpose are ones based on infrared absorption spectroscopy. Devices using carbon dioxide sensors of this type are described for example in EP-A 392 503, DE-A 35 33 557 and DE-A 31 37 258.

Devices are also known in which the $CO_2$ content is indicated as a colour change on an indicator system. Such devices are described for example in U.S. Pat. No. 4,728,499 and are available commercially.

The $CO_2$ detectors based on IR absorption spectroscopy have the advantage that they have a very rapid response time and reproduce the $CO_2$ content in the exhaled air with very high resolution. Such devices are extremely expensive, however, and their use, particularly in emergency medicine, for example in ambulances, is generally not possible for reasons of cost. $CO_2$ detectors based on a colour indicator reaction are admittedly less expensive, but they do not provide any trend information and, since colour comparisons are required, they are relatively imprecise and difficult to read off. Nor is it possible to record capnograms using $CO_2$ detectors based on a colour indicator reaction.

There is a real need in medicine for an inexpensive device for determining the carbon dioxide content in respiratory air. The method is meant to function per breath, that is to say that the carbon dioxide content (i.e. the carbon dioxide partial pressure) is meant to be determined in the inhaled air and in the exhaled air upon each respiratory cycle. The method is meant to be able to indicate a trend curve, or at least trend information, that is to say to indicate whether the maximum carbon dioxide content in the exhaled air decreases, increases or remains the same in successive respiratory cycles, and at what speed this occurs. There is also a need for a device for carrying out such a method.

A method for determining carbon dioxide production in respiratory gas is known from DE-A 40 01 803. The intention is to dispense with a device for measuring carbon dioxide concentration. In this method, in a serial measurement cycle, two oxygen sensors are used first to measure the oxygen consumption and the oxygen concentration values, with and without $CO_2$ absorber, and from these values, and from the oxygen concentration in the inhalation branch, the carbon dioxide production is then calculated in the control unit. The carbon dioxide content or carbon dioxide partial pressure in the exhaled air cannot be measured per breath using the device described in DE-A 40 01 803, and a corresponding method is not the subject of said publication. The determination of carbon dioxide production in respiratory gas as described in DE-A 40 01 803 must not be confused with the subject of the present invention which is not concerned with carbon dioxide production, but with the carbon dioxide content in the exhaled air, which must be determined per breath.

SUMMARY OF THE INVENTION

It is an object of the invention to make available a method and a device for determining the carbon dioxide content in respiratory air, which does not have the problems of the prior art and which in particular is so inexpensive that it can also be readily employed in ambulances and emergency medical vehicles and yet supplies reliable information on the absolute value and, above all, also on the trend of the carbon dioxide content in the respiratory air over several respiratory cycles.

This object is achieved by the subject matter of the patent claims.

The method according to the invention is based on using a rapid oxygen sensor to determine the oxygen partial pressure during breathing. The oxygen partial pressure can then be used to draw conclusions concerning the carbon dioxide content in the respiratory air. If, for example, the oxygen partial pressure in the inhaled air is 21 kPa and the oxygen partial pressure in the exhaled air falls to 16 kPa, the difference in the oxygen partial pressure of 5 kPa corresponds on first approximation to the maximum value of the carbon dioxide partial pressure in the exhaled air. By continuously measuring the oxygen partial pressure in the respiratory air, curves can be obtained which are the inverse of those shown for example in FIG. 1, and it is possible, by simple conversion, to obtain and record capnograms.

In a preferred simpler and less expensive embodiment, which is conceived in particular for use in ambulances and emergency medical vehicles, the whole capnogram is not recorded and displayed, instead only the maximum value of the carbon dioxide content in the exhaled air is determined and displayed per breath. In addition, the maximum value of the carbon dioxide content in the exhaled air is compared on each respiratory cycle with the previous respiratory cycles, and trend information is displayed, that is to say information on whether the maximum value of the carbon dioxide content in the exhaled air rises, falls or remains constant from respiratory cycle to respiratory cycle. Depending on this information, the operating personnel can then initiate appropriate measures or ask for detailed tests to be carried out.

DETAILED DESCRIPTION OF THE PREFERRED EMBODIMENTS

Figure 1A:
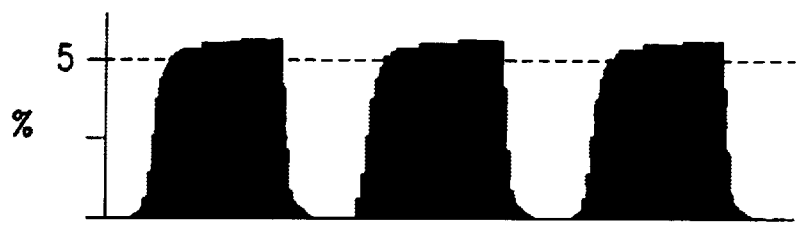
FIG. 1a shows the capnogram of a healthy patient under controlled ventilation.
Figure 1B:
FIG. 1b shows the capnogram of a patient in whom normal CO2 curve falls to 0 from one breath to the next.
Figure 1C:
FIG. 1c shows a rapid and constant fall of the $CO_2$ content in the exhaled air
Figure 1D:
FIG. 1d shows a sudden fall of the $CO_2$ content in the exhaled level to a lower level, but not to 0, and remains constant at said level.
Figure 2A:
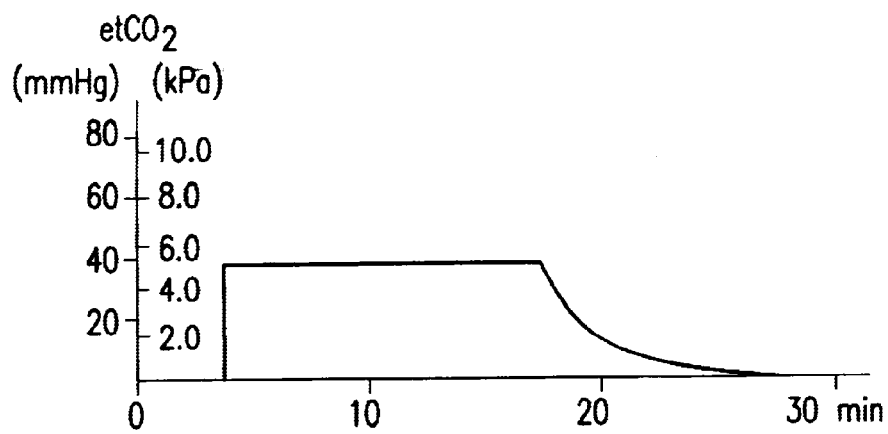
FIG. 2a shows a trend curve in which the patient is initially stable and the maximum content of the $CO_2$ in the exhaled air is about 5%.
Figure 2B:
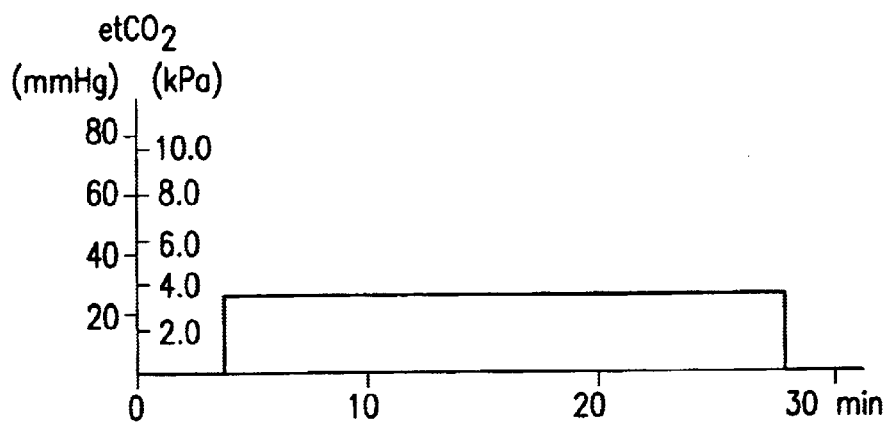
FIG. 2b shows a constantly low maximum $CO_2$ content in the exhaled air, at just under 4%.
Figure 2C:
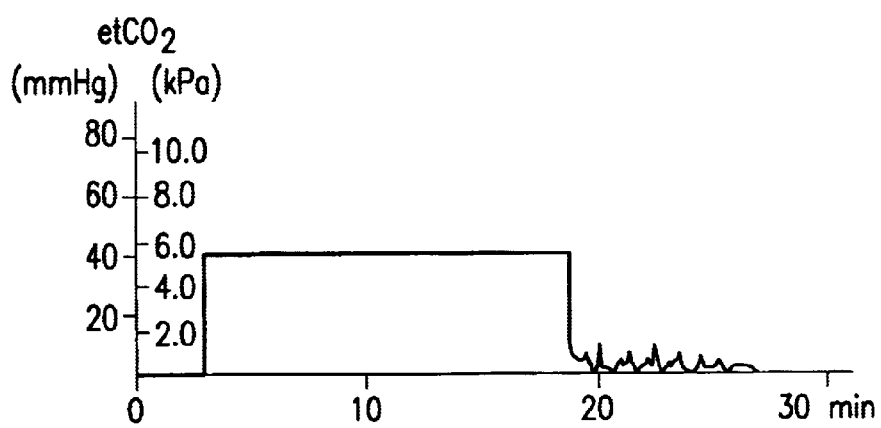
FIG. 2c shows a sudden fall in the maximum value of $CO_2$ in the exhaled air to about 0.
Figure 2D:
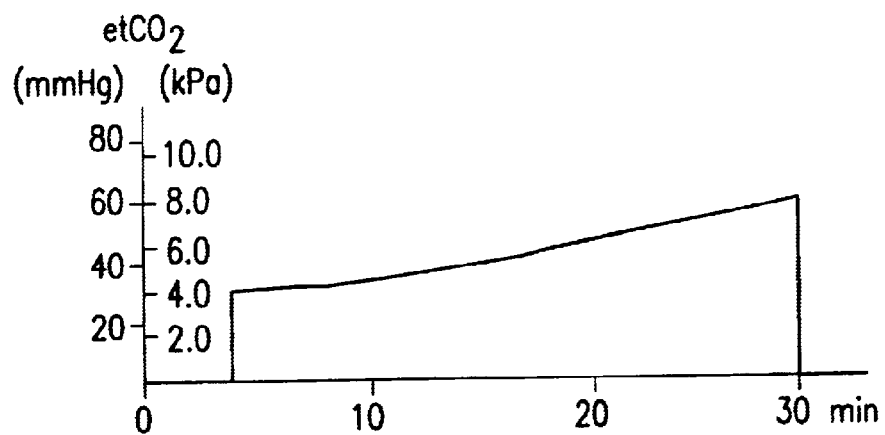
FIG. 2d shows a gradual rise in the maximum value of the $CO_2$ concentration in the exhaled air
Figure 2E:
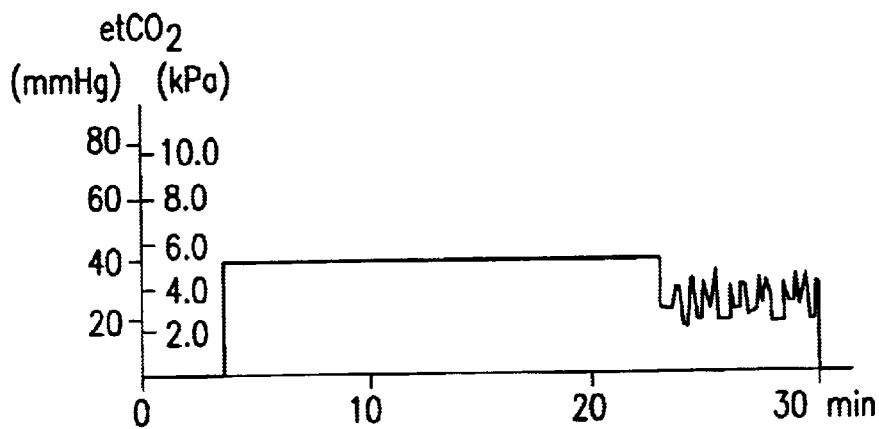
FIG. 2e shows the trend curve in the case of a sudden drop in the maximum value of the $CO_2$ content in the exhaled air.
Figure 2F:
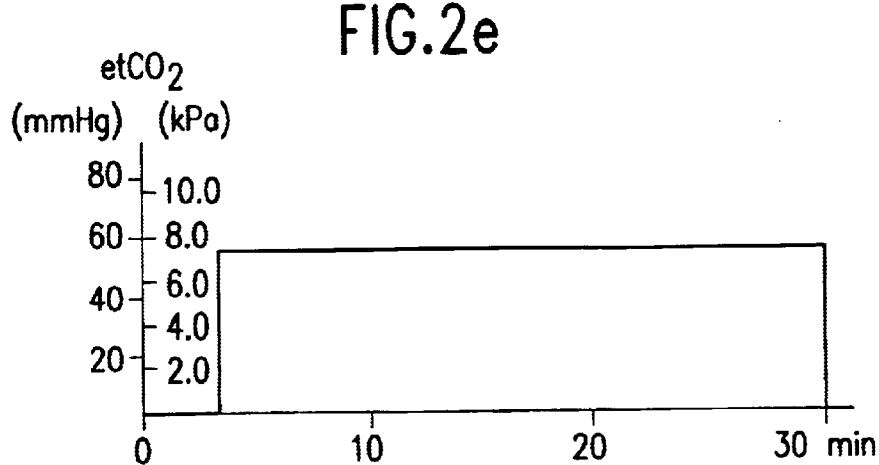
FIG. 2f shows a constantly high maximum value of the $CO_2$ in the exhaled air.

Any known ventilation device can in principle be adapted in such a way that it can be used to carry out the method according to the invention. For this purpose, an adapter is arranged on a known ventilation device, and an oxygen sensor is connected via this adapter. Since, according to the invention, only the oxygen content (oxygen partial pressure) or carbon dioxide content (carbon dioxide partial pressure) in the exhaled air is determined, and not the carbon dioxide production or the oxygen consumption, only an oxygen sensor connected to the ventilation device is needed to carry out the method according to the invention. Complicated measuring equipment and adjustment devices and the use of a plurality of oxygen sensors, mixing chambers or $CO_2$ absorbers, required for determining carbon dioxide production, are not required according to the invention and are not present in the devices according to the invention.

An oxygen sensor which is as rapid as possible should be used for the method according to the invention and the device according to the invention. Oxygen sensors with a response time of less than 500 milliseconds are preferred, in particular those with a response time of less than 200 milliseconds. Oxygen sensors with a response time of about 100 milliseconds or less are especially preferred. The faster the response time of the oxygen sensor, the better the resolution with which the capnogram can be recorded and the more extensive and more precise the information available to the operating personnel. The faster the response time of the oxygen sensor, the more precise the determination of the minimum value of the oxygen partial pressure in the exhaled air, that is to say the maximum value of the carbon dioxide partial pressure in the exhaled air.

Rapid oxygen sensors suitable for the method according to the invention are known and are available commercially. Such oxygen sensors are also already used in medicine, but not as yet for determining per breath the carbon dioxide content in respiratory air. Galvanic, paramagnetic or optical oxygen sensors can be mentioned here by way of example. Oxygen sensors which operate with laser diodes are also known. For cost reasons, however, a rapid electrochemical oxygen sensor is preferred according to the invention, such as is marketed by the company Teledyne Analytical Instruments and by the Applicant.

According to the invention, the oxygen sensor can in principle be arranged at any desired position on the ventilation device, but the measurement should preferably be carried out as close to the body as possible. Either the ventilation device already has an adapter piece to which the oxygen sensor can be connected, or an adapter piece for the oxygen sensor is applied to an attachment which is already present. A ventilation device can contain a patient tube through which a patient is artificially ventilated, but also a breathing mask which is often used in ambulances and emergency medical vehicles.

The method according to the invention and the device according to the invention can be used both in artificial ventilation of the patient and also in spontaneous ventilation.

The oxygen sensor can be connected to an evaluation and display device which calculates and displays the complete capnogram. Alternatively, and in a preferred embodiment of the invention, the evaluation and display device can also determine only the minimum value of the oxygen partial pressure or oxygen content and thus the maximum value of the $CO_2$ content or the $CO_2$ partial pressure in the exhaled air, calculate trend information and display both. The trend information can be represented as a diagram, as is shown for example in FIG. 2, or by other suitable optical and/or acoustic means, for example an arrow, whose angle of inclination from the horizontal indicates a rise or fall of the maximum value of the carbon dioxide content in the exhaled air, if appropriate in combination with an acoustic alarm if a rise or fall of the maximum value of the carbon dioxide content in the exhaled air exceeds a certain limit value.

To improve the noise, it is of course also possible for the evaluation device to calculate the mean over a number of breaths and display the mean value and/or to use it to calculate the trend information.

Evaluation and display devices which can suitably process and present the electrical signals supplied by oxygen sensors are known in principle and can be adapted in a conventional manner by a skilled person and integrated in the ventilation device according to the invention.

By measuring the absolute pressure, it is of course possible to normalize the measurement signal pressure and thereby allow the device to be used in airplanes or emergency helicopters.

In the context of this application, it is assumed that the exhaled air has a temperature of 37° C. and a relative humidity of 100%. To improve the measurement accuracy, the device according to the invention can be fitted with temperature and/or humidity sensors which determine the temperature and/or humidity of the inhaled air and/or the exhaled air. The oxygen partial pressure measured according to the invention or the carbon dioxide partial pressure calculated from this can then be corrected in a manner known per se, to minimize the measurement error, in accordance with the actual measured temperature and humidity values.

In the above description, it is assumed that the air mixture delivered to the patient consists substantially of oxygen and otherwise inert gases such as nitrogen.

Should the patient be ventilated with a gas mixture which contains non-inert constituents, the values for carbon dioxide partial pressure calculated with the method according to the invention must be corrected in respect of the non-inert gas components. In practice, this occurs in particular when a patient is ventilated with a gas mixture containing an anaesthetic gas. In this case, the partial pressure of the anaesthetic gas in the inhaled air and in the exhaled air must be determined and taken into consideration when determining the carbon dioxide partial pressure from the measured oxygen partial pressure. In the preferred embodiment of the method according to the invention in emergency medicine, this difficulty does not arise.

The invention is described in more detail below with reference to FIG. 3.

Figure 3:
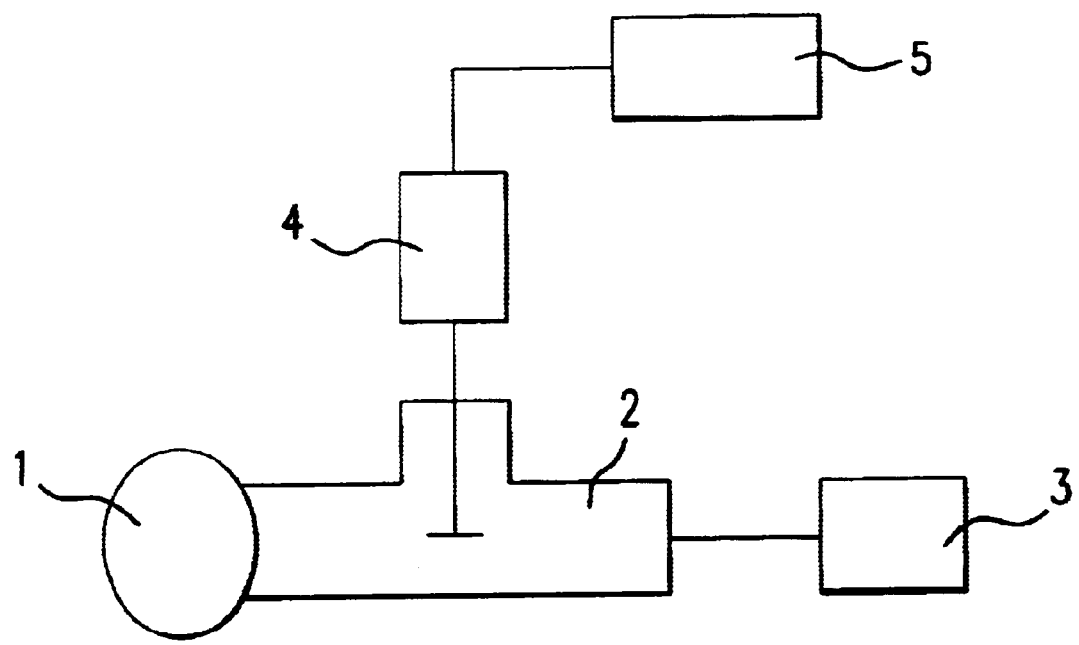
FIG. 3 is a schematic of a preferred embodiment of a device for carrying out the method according to the invention.

FIG. 3 is a diagrammatic representation of a preferred embodiment of a device for carrying out the method according to the invention. In FIG. 3, reference number 1 designates a breathing mask which is placed on the patient's mouth and nose. Reference number 2 represents an adapter piece on the breathing mask near the patient for application of an oxygen sensor for carrying out the method according to the invention. Reference number 3 represents further known components of a ventilation device which are not relevant to the present invention and whose specific design depends on the specific ventilation device. Reference number 4 indicates the oxygen sensor, reference number 5 the evaluation and display device connected to the oxygen sensor. In an alternative embodiment, reference number 1 designates not a breathing mask, but a patient tubing for ventilating a patient. Likewise, the adapter piece 2 and the breathing mask/patient tubing 1 can be in one piece.

When carrying out the method according to the invention, the breathing mask 1 is placed over the patient's mouth and nose. As the patient breathes, the rapid oxygen sensor 4 first measures, over one respiratory cycle, the oxygen partial pressure (or oxygen content) of the gas mixture delivered to the patient's lungs, then the oxygen content (or oxygen partial pressure) in the exhaled air. The difference in the two oxygen values corresponds substantially to the carbon dioxide present in the exhaled air when, assuming the conditions set out above, a simple conversion is carried out. The corresponding calculations are carried out in the evaluation and display device 5 and the carbon dioxide value is presented directly on the evaluation and display device 5. The method is carried out continuously so that, at the next respiratory cycle, the oxygen content of the oxygen-containing gas mixture entering the patient's lungs is once again determined and the oxygen content in the exhaled air is again determined accordingly. In a preferred embodiment, the evaluation and display device determines the maximum of the carbon dioxide content in the exhaled air and displays this value. It is possible to display a mean value of the maximum carbon dioxide content determined over several respiratory cycles. A trend display on the display device shows whether the carbon dioxide content rises, falls or remains constant over time.

With good resolution of the oxygen sensor, the electrical signals delivered to the evaluation unit from the oxygen sensor are inverse to the curves in FIG. 1. The evaluation unit inverts the data and then displays either the complete capnogram or the maximum value of the carbon dioxide content and the trend information.

What is claimed is:

1. A method for determining carbon dioxide content in respiratory air per breath, comprising:

(a) continuously determining oxygen partial pressure in respiratory air using an oxygen sensor, wherein the oxygen sensor determines a minimum value of the oxygen partial pressure in exhaled air per respiratory cycle; and (b) determining, as a maximum value of carbon dioxide in exhaled air, the absolute value of the difference between the minimum value of the oxygen partial pressure in exhaled air and the oxygen partial pressure in inhaled air.

2. The method of claim 1, wherein the maximum value of carbon dioxide in the exhaled air is compared over several respiratory cycles and change(s) in the maximum value of carbon dioxide in the exhaled air over several respiratory cycles indicates trend information.

3. The method of claim 1, wherein the oxygen sensor has a response time of not more than 500 milliseconds.

4. The method of claim 1, wherein the oxygen sensor is an electrochemical oxygen sensor.

5. A device for determining carbon dioxide content in respiratory air per breath, comprising:

(a) an oxygen sensor to continuously determine oxygen partial pressure in respiratory air, wherein the minimum value of the oxygen partial pressure in exhaled air is determined upon each respiratory cycle; and (b) means to determine the absolute value of the difference between the instantaneous oxygen partial pressure in exhaled air and the oxygen partial pressure in inhaled air, wherein the absolute value is defined as the carbon dioxide content of the respiratory air;

wherein in (b), the means to determine the absolute value determines the difference between the minimum value of the oxygen partial pressure in the exhaled air and the oxygen partial pressure in the inhaled air such that the maximum value of carbon dioxide in the exhaled air is determined.

6. The device of claim 5, comprising a breathing mask.

7. The device of claim 5, further comprising ventilation tubing.

* * * * *